(12) United States Patent
Chenaux

(10) Patent No.: US 11,812,976 B2
(45) Date of Patent: Nov. 14, 2023

(54) OFFSET REAMER DRIVER WITH REMOTE RELEASE MECHANISM

(71) Applicant: Incipio Devices SA, St-Blaise (CH)

(72) Inventor: Fabrice Chenaux, Cortaillod (CH)

(*) Notice: Subject to any disclaimer, the term of this patent is extended or adjusted under 35 U.S.C. 154(b) by 0 days.

(21) Appl. No.: 16/761,824

(22) PCT Filed: Nov. 7, 2018

(86) PCT No.: PCT/IB2018/058749
§ 371 (c)(1),
(2) Date: May 6, 2020

(87) PCT Pub. No.: WO2019/092615
PCT Pub. Date: May 16, 2019

(65) Prior Publication Data
US 2021/0196287 A1    Jul. 1, 2021

Related U.S. Application Data

(60) Provisional application No. 62/593,277, filed on Dec. 1, 2017, provisional application No. 62/582,357, filed on Nov. 7, 2017.

(51) Int. Cl.
*A61B 17/16* (2006.01)
*A61B 17/00* (2006.01)

(52) U.S. Cl.
CPC ...... *A61B 17/1624* (2013.01); *A61B 17/1631* (2013.01); *A61B 17/1666* (2013.01); *A61B 2017/00477* (2013.01); *A61B 2017/00738* (2013.01)

(58) Field of Classification Search
CPC ............ A61B 17/1664; A61B 17/1666; A61B 17/1624; A61B 17/1628; A61B 17/1631
See application file for complete search history.

(56) References Cited

U.S. PATENT DOCUMENTS

| 7,217,271 | B2  |   | 5/2007  | Wolford et al. |              |
|-----------|-----|---|---------|----------------|--------------|
| 9,078,672 | B1  | * | 7/2015  | Rosse          | A61B 17/1631 |
| 11,160,565| B2  | * | 11/2021 | Biegun         | A61B 17/1631 |
| 2005/0124981 | A1 |  | 6/2005 | Desarzens et al. |           |

(Continued)

FOREIGN PATENT DOCUMENTS

| WO | 2006061708 A2 | 6/2006 |
| WO | 2017029546 A2 | 2/2017 |

OTHER PUBLICATIONS

International Search Report, International Patent Application No. PCT/IB2018058749, dated Apr. 23, 2019.

*Primary Examiner* — Matthew J Lawson
(74) *Attorney, Agent, or Firm* — John Moetteli; Da Vinci Partners LLC

(57) ABSTRACT

A system, method and/or reamer driver device provides a driver which has a mean for remotely connect or disconnect (release) the reamer without having to manipulate a release sleeve located close to the surgical tool connector. The surgical reamer driver has a transmission drive train, a housing assembly enclosing the transmission drive train and a locking surgical tool connector. The driver further includes a device for remotely inducing relative movement of the transmission drive assembly with respect to at least a portion of the housing assembly to activate locking and unlocking of the locking surgical tool connector.

26 Claims, 14 Drawing Sheets

(56) References Cited

U.S. PATENT DOCUMENTS

| | | | |
|---|---|---|---|
| 2005/0159751 A1* | 7/2005 | Berthusen | A61B 17/1666 |
| | | | 606/80 |
| 2006/0217728 A1* | 9/2006 | Chervitz | A61B 17/1757 |
| | | | 606/79 |
| 2008/0058804 A1* | 3/2008 | Lechot | A61B 17/1631 |
| | | | 606/53 |
| 2008/0287952 A1* | 11/2008 | Mcminn | A61B 17/1631 |
| | | | 606/80 |
| 2017/0304078 A1 | 10/2017 | Chenaux | |
| 2018/0049753 A1* | 2/2018 | Chenaux | A61B 50/30 |
| 2018/0206857 A1* | 7/2018 | Chenaux | A61B 17/162 |
| 2020/0163683 A1* | 5/2020 | Anderson | A61B 17/1633 |
| 2022/0218362 A1* | 7/2022 | Anderson | A61B 17/162 |

\* cited by examiner

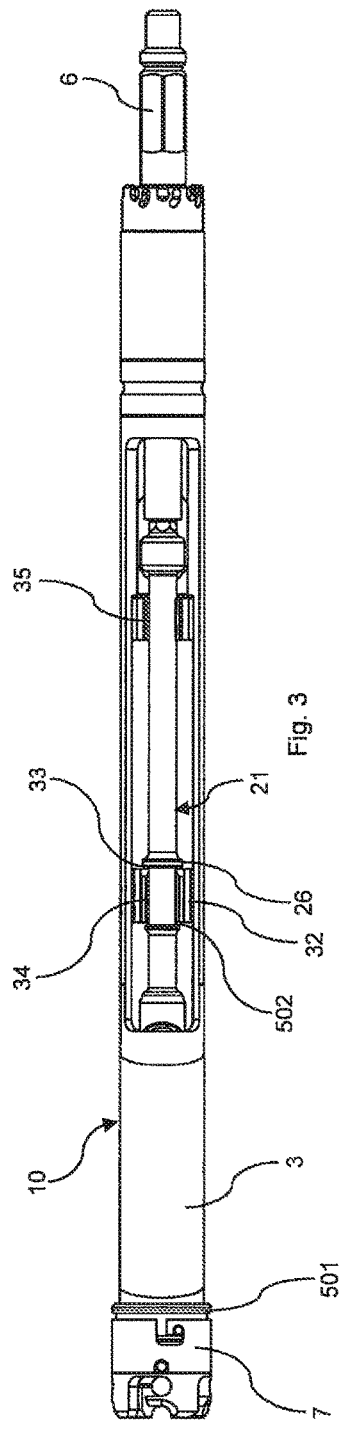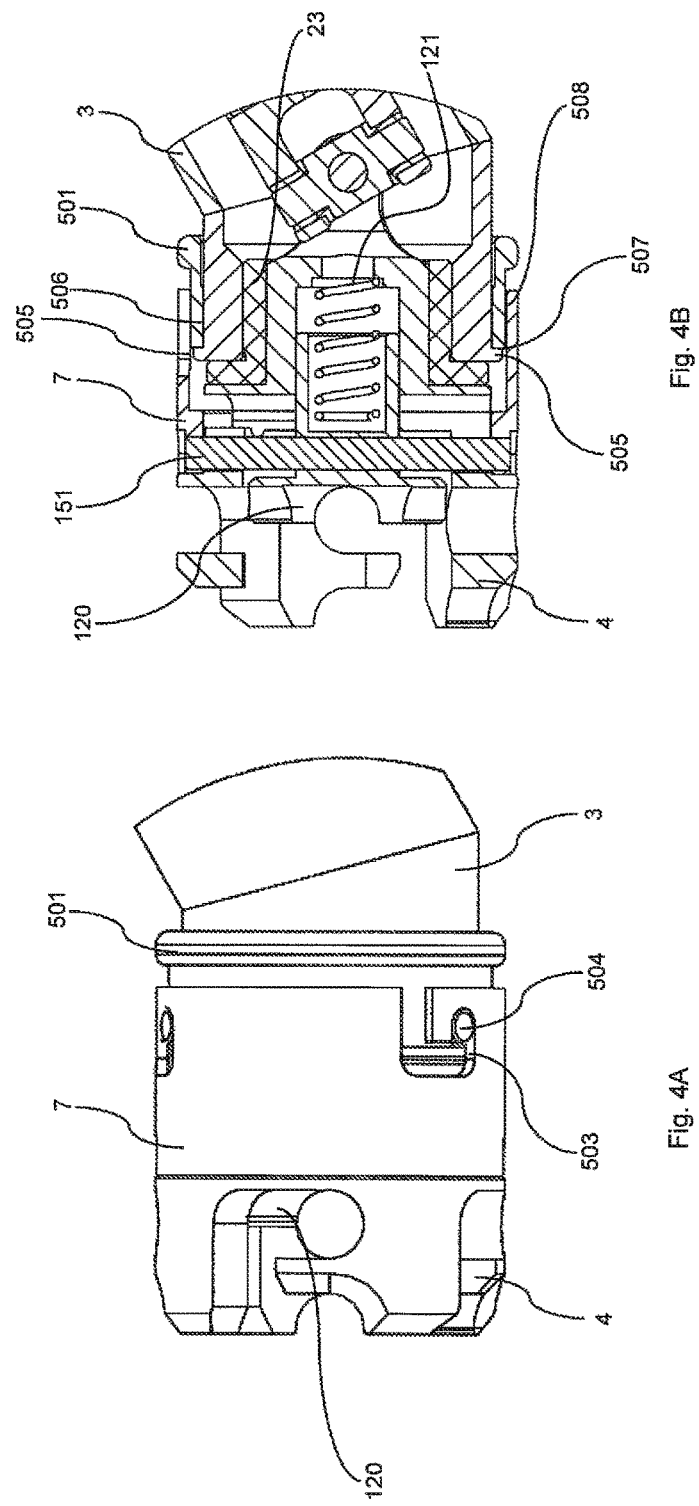

OFFSET REAMER DRIVER WITH REMOTE RELEASE MECHANISM

CROSS REFERENCE TO RELATED APPLICATIONS

This application is the National Stage of International Application No. PCT/IB2018/058749, filed Nov. 7, 2018, which claims benefit under 35 USC § 119(a), to U.S. provisional patent application Ser. No. 62/582,357, filed Nov. 7, 2017 and U.S. provisional patent application Ser. No. 62/593,277, filed Dec. 1, 2017.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

BACKGROUND OF THE INVENTION

This invention relates to a reamer driver suitable constructed to be used to reshape acetabular. Often, the distal end of the reamer driver is engulfed in soft tissue. It is therefore difficult to access the distal end. Prior art devices in which locking and unlocking of the reamer is effected by acting on an actuator at the distal end are therefore sometimes difficult to use.

There exists therefore a need for a reamer driver to remotely connect or release the reamer without having to manipulate a release sleeve located in the close area of the surgical tool connector.

SUMMARY OF THE INVENTION

A system, method and/or reamer driver device provides a driver which has a means for remotely connect or disconnect (release) the reamer without having to manipulate a release sleeve located close to the surgical tool connector. The surgical reamer driver has a transmission drive train, a housing assembly enclosing the transmission drive train and a locking surgical tool connector. The driver further includes a device for remotely inducing relative movement of the transmission drive assembly with respect to at least a portion of the housing assembly to activate locking and unlocking of the locking surgical tool connector.

An object of the invention is to provide a driver which has a means for remotely connecting or disconnecting (releasing) the reamer without having to manipulate a release sleeve located close to the surgical tool connector.

Another object of the invention is to provide a driver which allows an easy replacement of components, e.g. when components are worn out.

Another object of the invention is to provide a reamer driver having a simple reamer driver connection that allows quick connect of different type of acetabular reamers from the center of the driver with a mechanism with no nooks or crannies that might trap or attract bone chips or debris. In comparison to the existing reamer driver connections described in the prior art, the locking mechanism located in the center of the driver of the present invention consists of a plate whose length in the axial direction allows for axial translation without revealing spaces in which debris or chips might enter, thereby preventing such debris and bone chips from jamming the mechanism. Chips and debris are highly undesirable as such may potentially disconnect the reamer from the reamer driver during use (during rotation). It also reduces soft tissue irritation while rotating by limiting the sharp edges of components located around the head of the reamer driver.

BRIEF DESCRIPTION OF THE DRAWINGS

The attached drawings represent, by way of example, different embodiments of the subject of the invention.

FIG. 3 is a top view of the housing assembly of the reamer driver, showing the transmission drive chain in a partially assembled state.

FIG. 4A is a detail of FIG. 3 showing the distal surgical tool connector assembly.

FIG. 4B is a partial cross-section view of FIG. 4A showing the surgical tool connector.

Figure 1A:
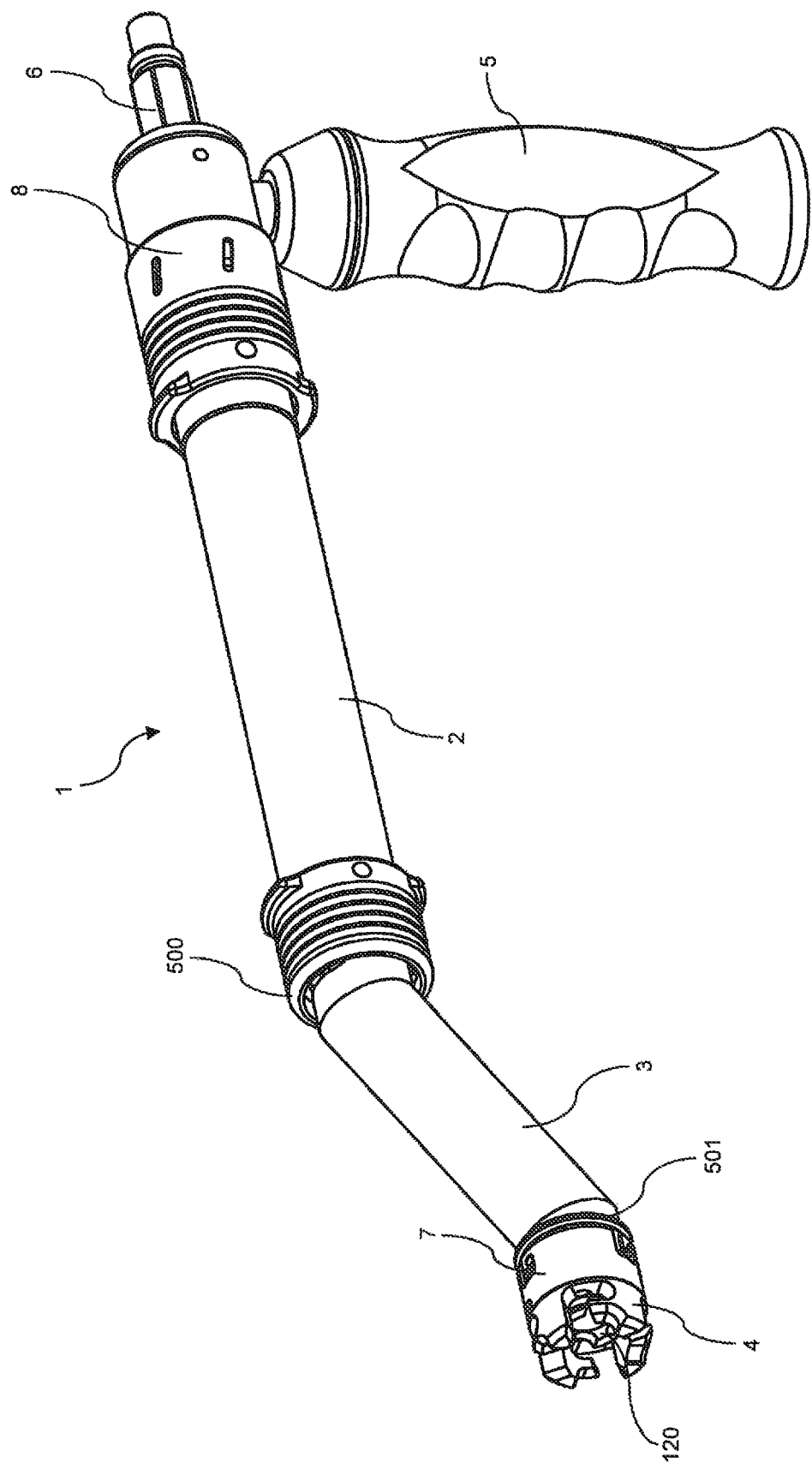
FIG. 1A is a perspective view of the fully assembled reamer driver.
Figure 1B:
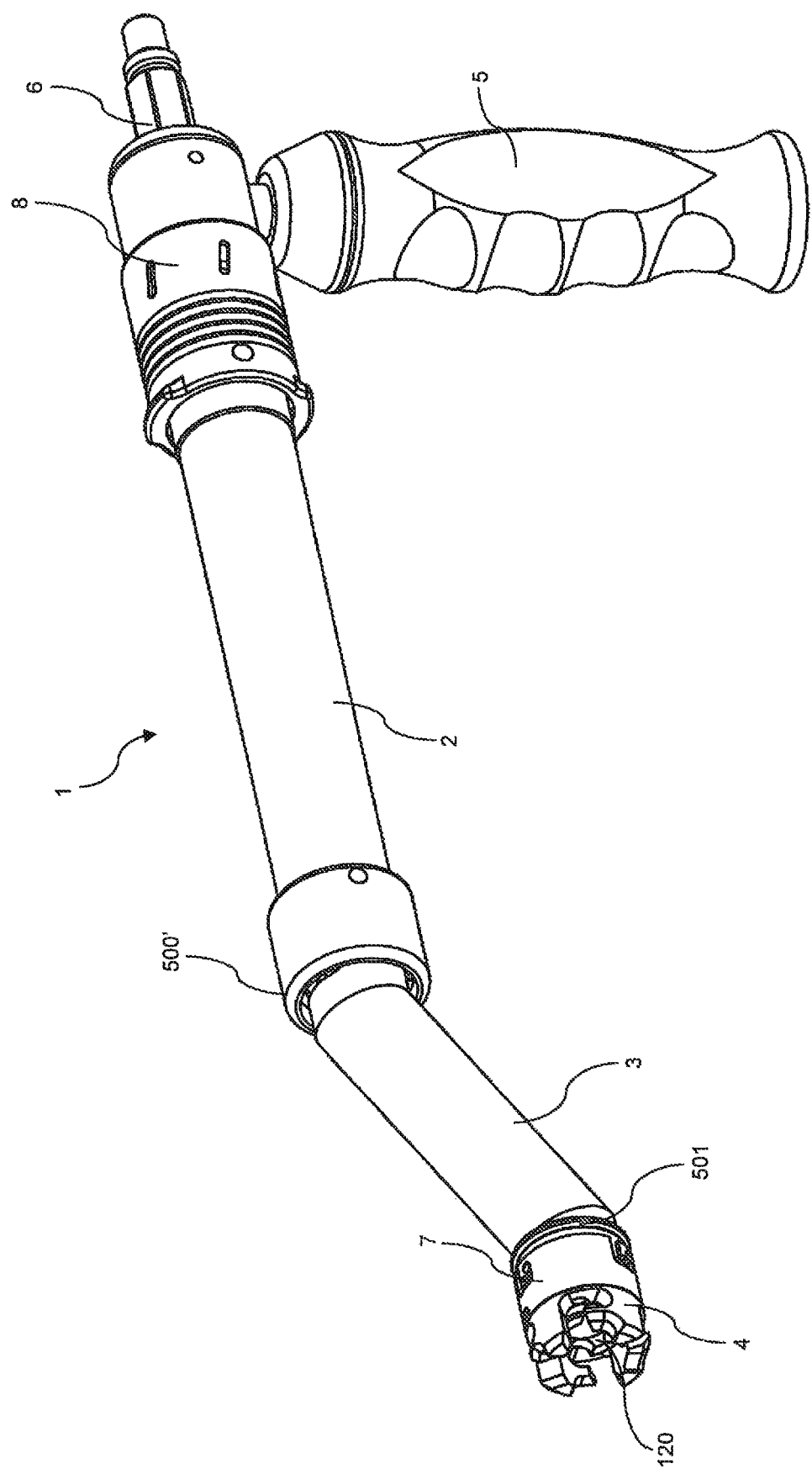
FIG. 1B is a perspective view of a second embodiment of the fully assembled reamer driver.
Figure 1C:
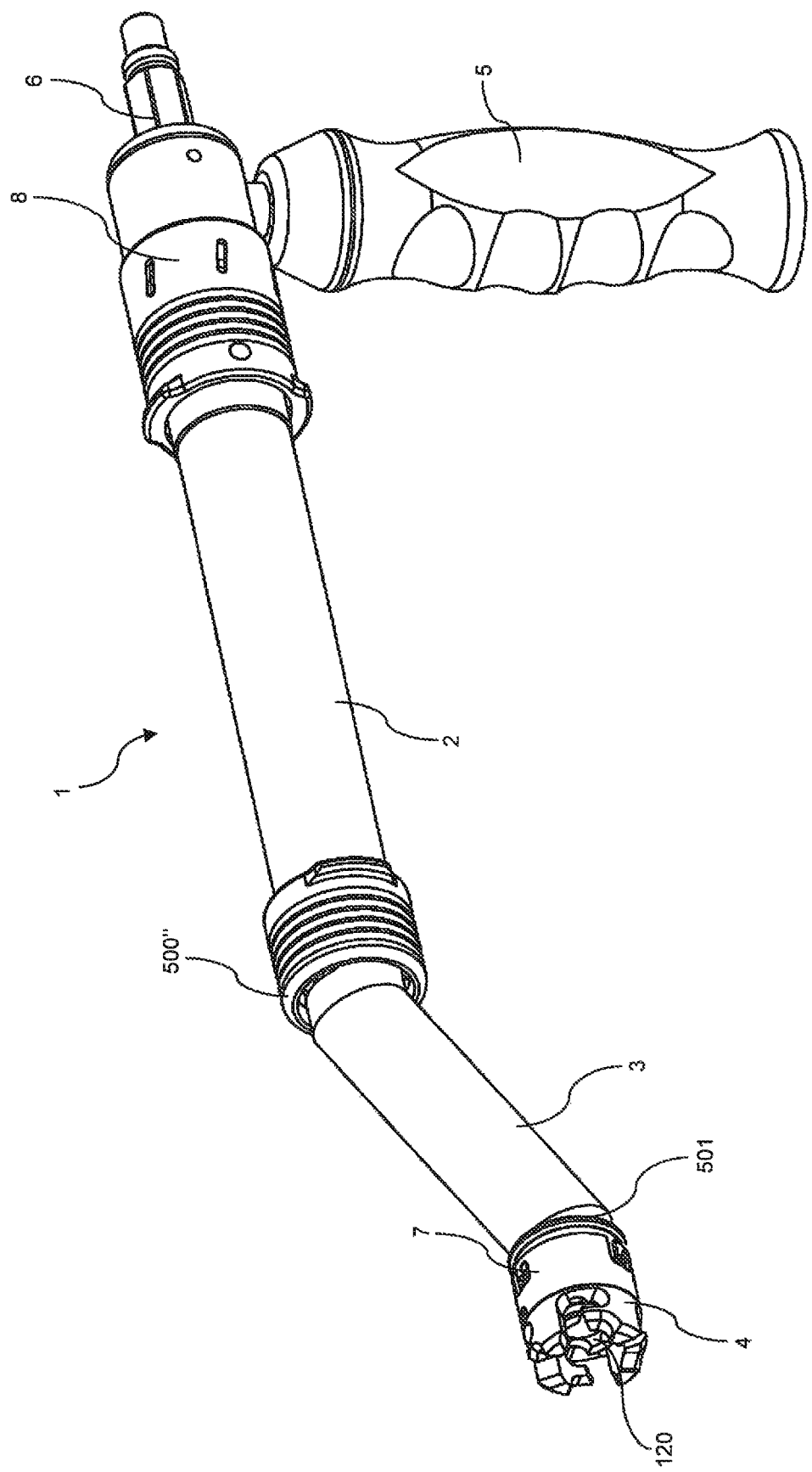
FIG. 1C is a perspective view of a third embodiment of the fully assembled reamer driver.
Figure 1D:
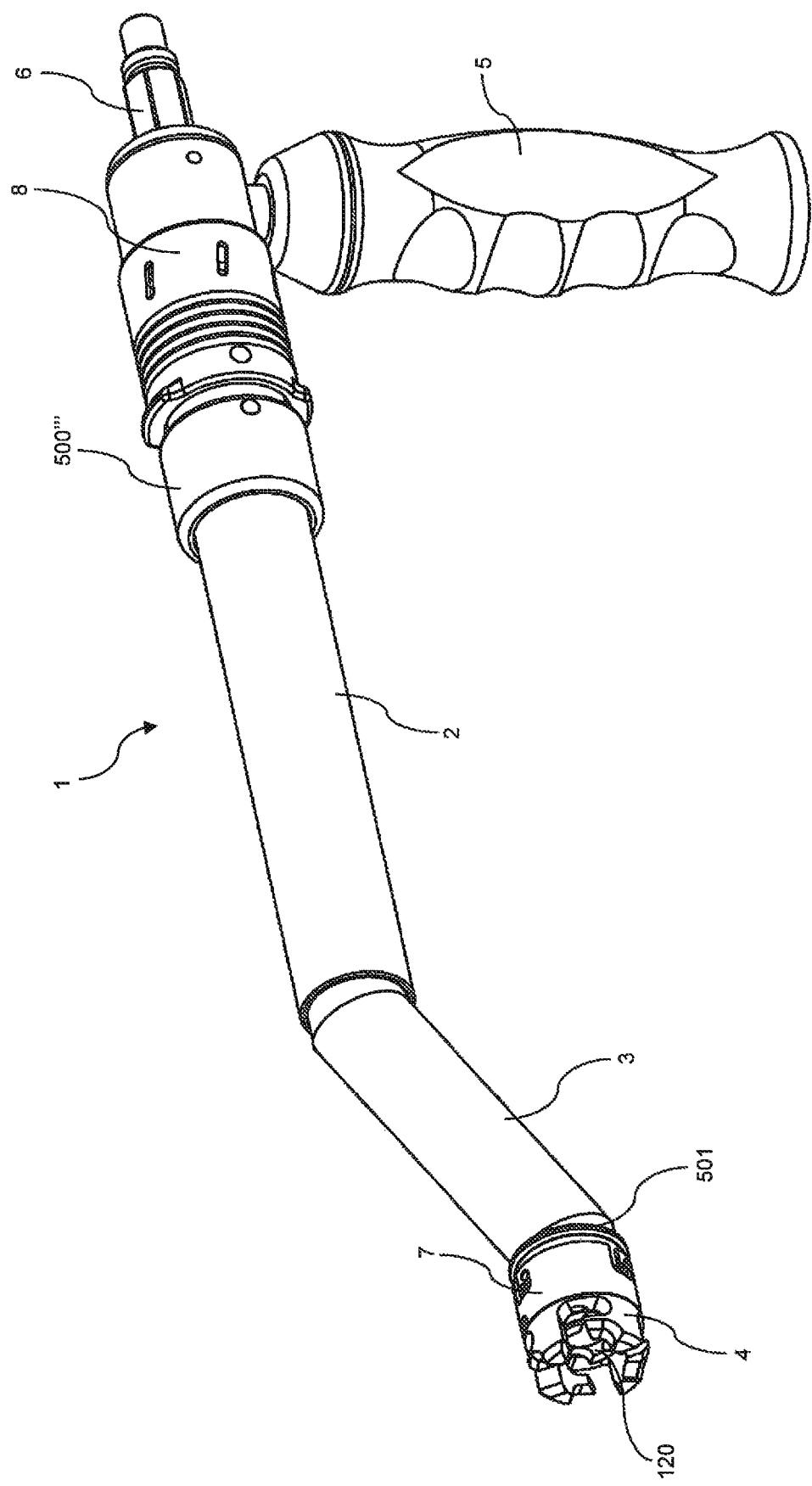
FIG. 1D is a perspective view of a fourth embodiment of the fully assembled reamer driver.
Figure 1E:
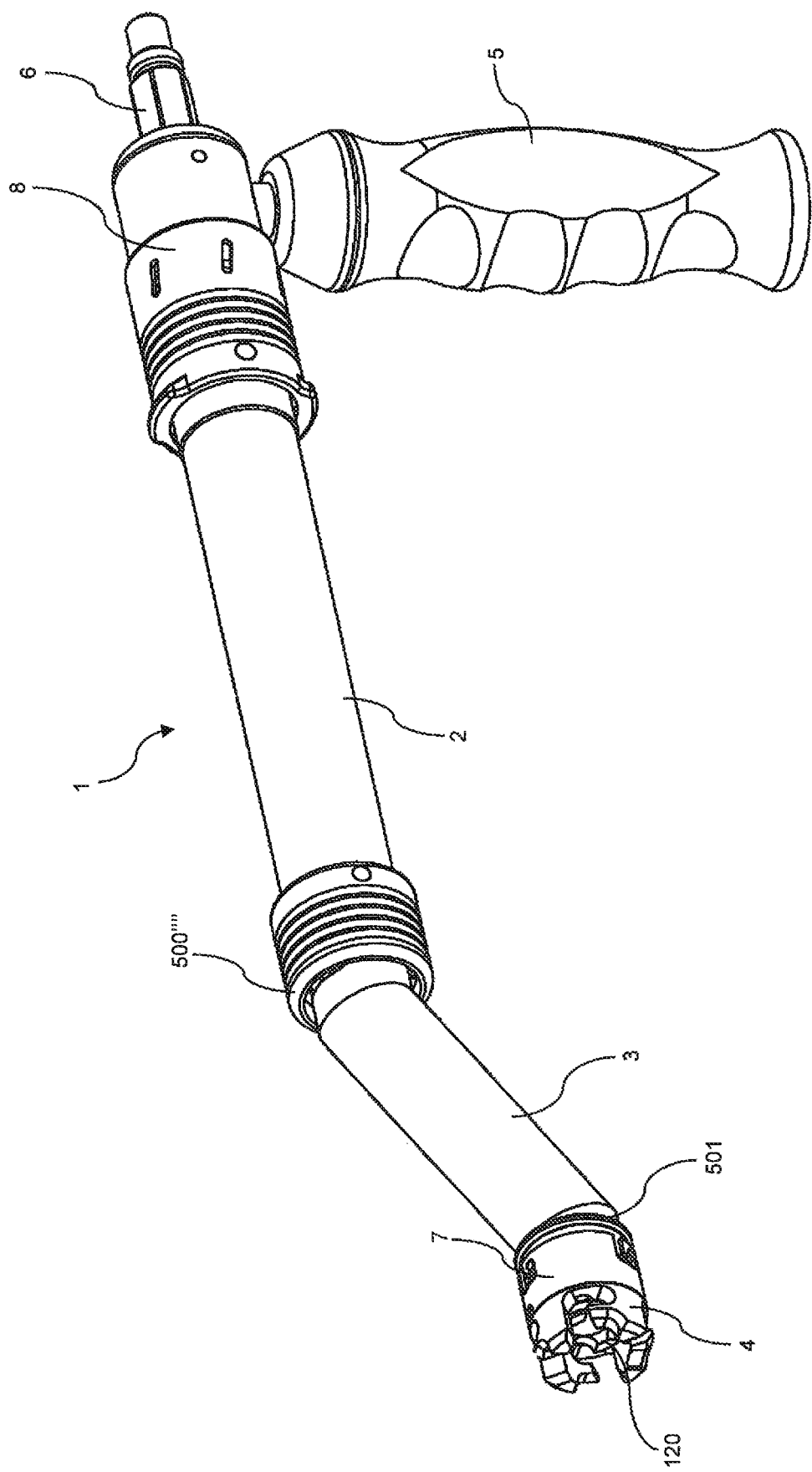
FIG. 1E is a perspective view of a fifth embodiment of the fully assembled reamer driver.

Those skilled in the art will appreciate that elements in the Figures are illustrated for simplicity and clarity and have been drawn to scale. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary embodiments disclosed herein without departing from the spirit and scope of the invention.

Referring to FIGS. 1A, 1B, 1C, 1D and 1E, different embodiments of the assembled reamer driver 1 are shown. Such a reamer driver 1 is a surgical instrument used to drive bone cutting tools during minimal invasive surgeries. A proximal tube 2 of the handle assembly 9 fully closes the top opening 30 of the body 10 (shown in FIG. 2). This tube 2 is part of the handle assembly 9. Housing body 10 preferably has a stretched and flattened. Z shape at position 3, where the central axis of the proximal transmission shaft 25 (power input) and the central axis of the distal transmission shaft 24 (power output) are not coincident. A quick tool connector/reamer head 4 is affixed to the distal transmission shaft 24. Bone cutting tools 227 (shown in FIG. 12) are connectable to the reamer head 4. Handle 5 is part of handle assembly 9. The handle 5 may be for example out of metal, plastic or silicone, and possess an anti-slip coating, and is preferably ergonomically shaped, with or without anti-slip profile. A motor shaft quick connection 6 allows the application of torque via a flex-shaft for example. A ring or sleeve 7, connected to the central cutting tool connection 120, allows the locking of a bone cutting tool 227 on the driver head 4. A remote release sleeve 500, sliding onto the proximal tube 2 of the handle assembly 9, permits the axial movement of the driver head 4 once actuated in order to release the one cutting tool. The bayonet sleeve SO1 retains the ring 7 from moving forward (distally or towards the reamer head 4) once assembled. The bayonet mechanism allows separation of the ring 7 and the bayonet sleeve 501 for disassembling of the instrument. The sleeve & allows the release of the handle assembly 9. One of the differences to the known prior art is that the device is fully encapsulated, avoiding penetration of debris and abrasion of soft tissues during use. The variant shown in the figures is made out of four main components, the transmission drive chain 21, the body 10, the motor shaft coupling 11 and the handle assembly 9.

Figure 2:
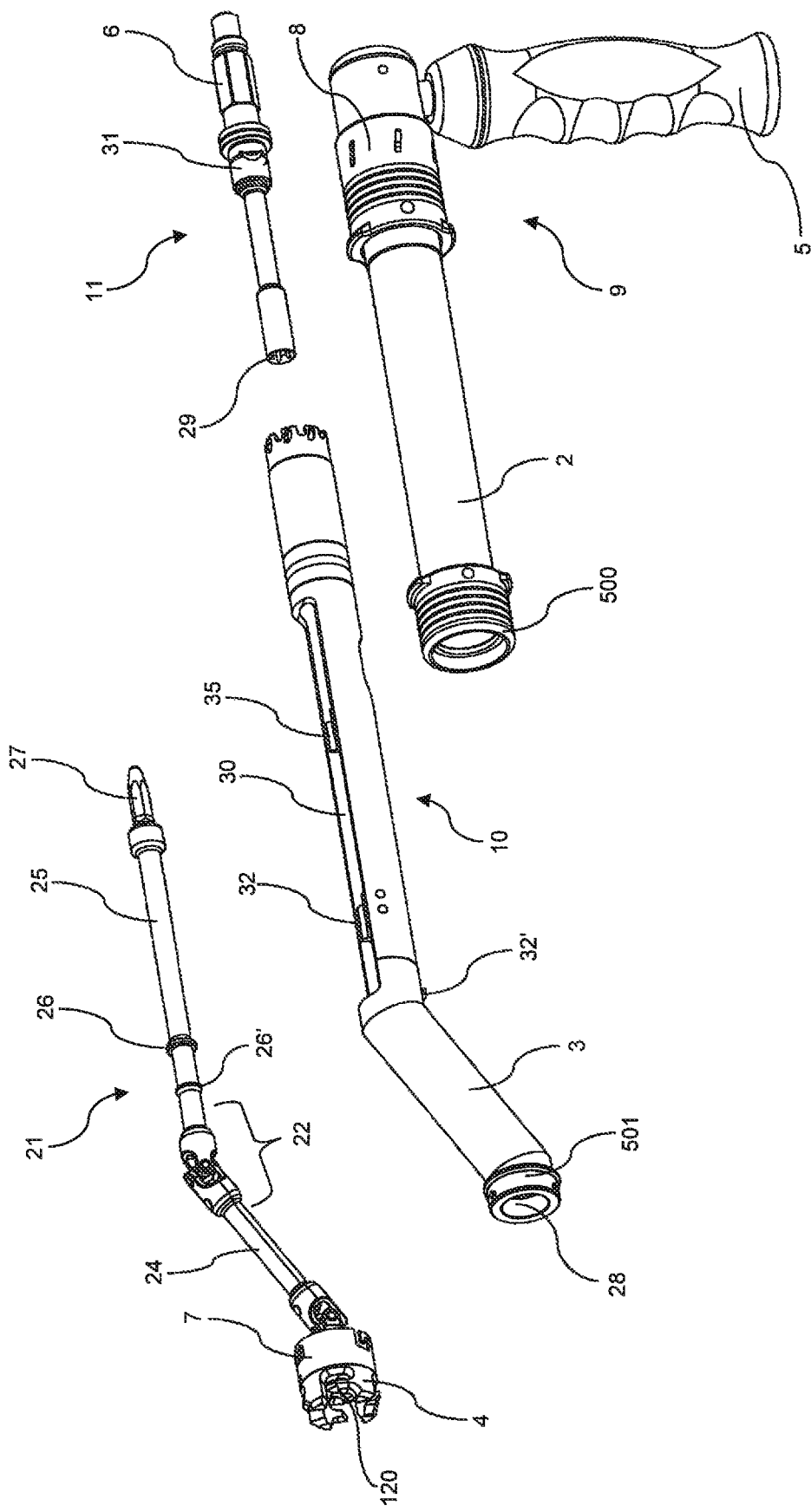
FIG. 2 is an exploding view of main components of the reamer driver.

Now referring to FIG. 2, the main components, namely, the transmission drive chain 21, the body 10, the motor shaft coupling 11 and the handle assembly 9, are shown separated from each other. Mechanical load applied on the handle 5 is transmitted through to the head bearing 23 and finally to the driver head 4. There is no transmission of load into the motor shaft coupling 11 as it is isolated from the bandle. The head bearing 23 may be made, for example, out of PEEK, carbon fiber PEEK, Teflon, PPSU, or metal. The transmission drive chain 21 typically includes universal joints 22, a distal transmission shaft 24, a proximal transmission shaft 25, stop rings 26 and 26' allowing the axially positioning of the transmission drive chain when inserted into the bearing(s) 32, 35. A first rotational transmission feature 27 (hex, square, triangle, any polygonal, extruded form) allows transmission of the rotational torque from the motor shaft coupling 11 to the transmission drive chain 21. This first feature 27 transmits only rotational torque but not the eventual axial force applied on the motor shaft coupling 11. A front opening 28 of the housing body 10 is located so that the transmission drive chain 21 can be inserted therein. A second rotational transmission feature 29 (hexagon, square, triangular, or any polygonal shape) is connectable to the first rotational transmission feature 27 and is free to slide axially into it. A top opening 30 of the housing assembly 10 provides clearance for the transmission drive chain 21 and is located where the transmission drive chain 21 exits during while inserting into the housing assembly 10 and before it reaches its assembled position. The motor shaft bearing 31 mounts between the motor shaft coupling 11 and the body 10, and may be made for example out of PEEK, carbon fiber PEEK, Teflon, PPSU or metal. One or more distal and proximal transmission drive chain bearing(s) 32, 35 support the transmission drive train 21 and may be made for example out of PEEK, carbon fiber PEEK, Teflon, PPSU or metal, having a snapping feature to capture the proximal transmission shaft 25 and maintain it in place. This transmission drive chain bearing(s) 32, 35 insures the axial positioning of the transmission drive chain with the stop ring 26 and 26'. A remote release sleeve 500 being part of the handle assembly 9 is able to move axially. The distal bearing 32 supports the proximal drive train shaft 25 and is able to move axially when actuated by the remote release sleeve 500 and therefore translate the transmission drive chain 21 axially by pressing against the externally disposed tang 32' thereof. The bayonet sleeve 501 is assembled onto the body 10 and able to move axially and rotate around the distal end of the body 3. Retained thereon by a flange 505 (shown in FIG. 4B).

Now referring to FIG. 3, the housing body 10 of the reamer driver 1 is assembled together with the transmission drive chain 21. A first point of contact 33 between the rear stop flange 26 and the distal transmission drive chain bearing 32 and a second point of contact 502 between the stop ring 26' and the distal transmission drive chain bearing 32 maintain the axial position of the transmission drive chain 21 in the distal bearing 32. A point of contact 34 between the proximal transmission shaft 25 and the bearing (s) 32, 35 insures the concentricity of the proximal transmission shaft 25 within the housing (e.g. tubes) of the housing body 10 and allows its rotation. The bayonet sleeve 501, once engaged and connected to the ring 7, retains the ring 7 from moving forward when the transmission drive chain 21 moves forward. Note that the bayonet sleeve 501 has bearing surfaces to ensure smooth rotation onto the distal end of the body 3.

Now referring to FIG. 4A, a detail of FIG. 3 and FIG. 4B showing a cross-section view of FIG. 4A, the surgical tool connector 4 is shown in its closed position. The bayonet sleeve 501 is engaged and connected into the ring 7 through pin(s) 504. The bayonet sleeve 501 rotates with the reamer head 4 and rides on a bearing surface 506. The bayonet sleeve 501 is retained against moving forward by a flange 505 being part of the body 3. Once engaged and connected to the ring 7, the bayonet sleeve 501 retains the ring 7 from moving forward when the transmission drive chain 21 moves forward. The pin 151 connects the ring 7 together with the central cutting tool connection 120. When the the transmission drive chain 21 slides backward/forward, the reamer driver head 4 slides backward/forward relatively to the housing assembly 3. Since the cutting tool locking mechanism (ring 7, pin 151 and central cutting tool connection 120) is maintained against the housing assembly 3 by the bayonet sleeve 501, it releases/locks the cutting tool. The cutting tool locking mechanism is spring loaded with spring 121 in its locked position. In a different embodiment, the bayonet sleeve 501 can be replaced by any means of connecting the ring 7 to the distal end of the body 3 in order to prevent it from moving forward when the transmission drive chain 21 moves forward. As an example, the connection could be a clip or a spring-loaded hook interacting with a groove located in the distal end of the body 3.

Figure 5:
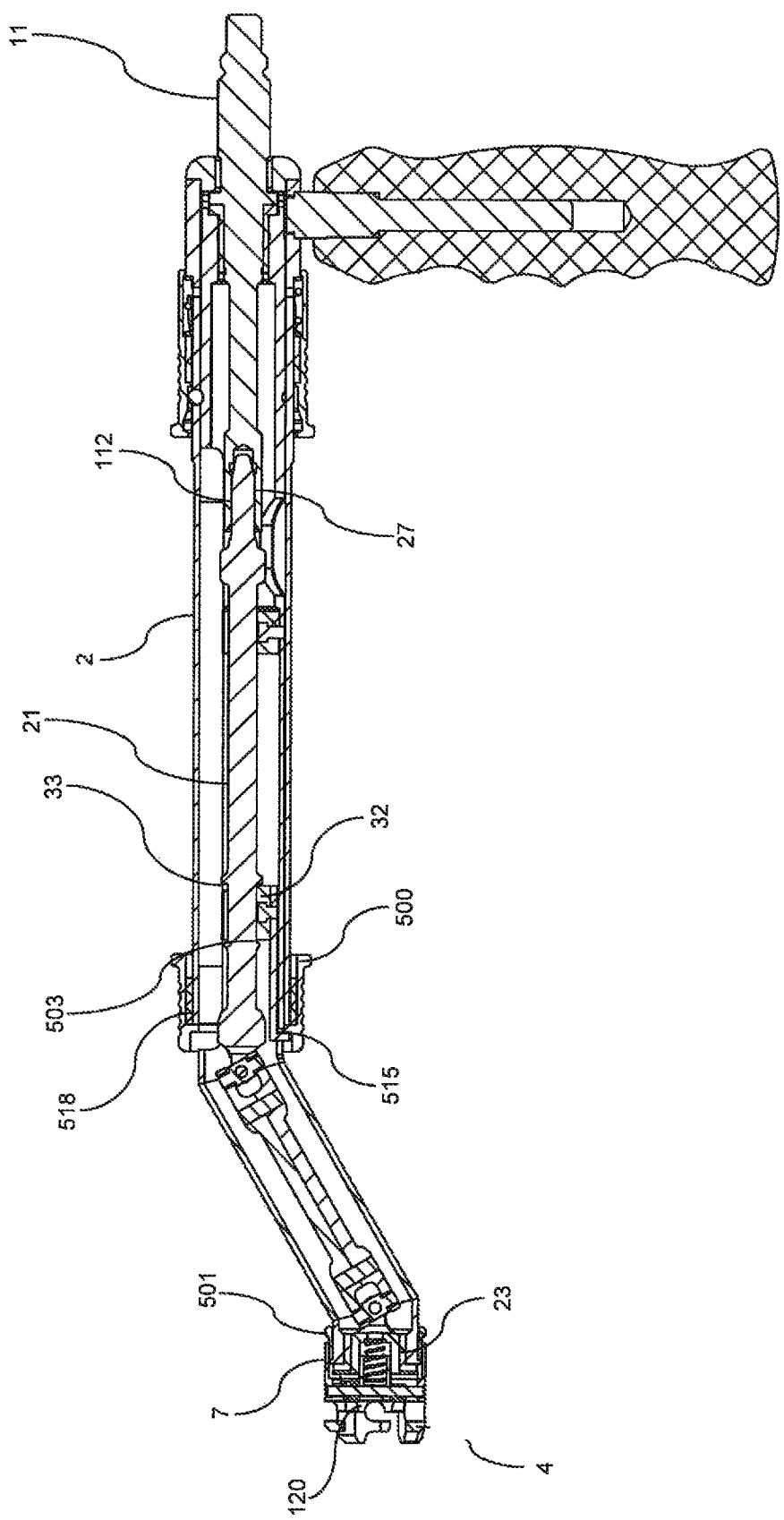
FIG. 5 is a cross-section view of the fully assembled reamer driver with the surgical tool connector in its closed position.

Now referring FIG. 5, the fully assembled reamer driver is shown with the surgical tool connector 120 in its closed position. The distal transmission drive chain bearing 32 is able to axially move when actuated by the remote release sleeve 500, through the contact point 515, and therefore drive the transmission drive chain 21 forward. A point of contact 112 of the rotational transmission feature 27 allows transmission of the rotational torque from the motor shaft coupling 11 to the transmission drive chain 21. This feature transmits only rotational torque but allows the proximal transmission shaft 25 to slide axially into it.

Figure 6:
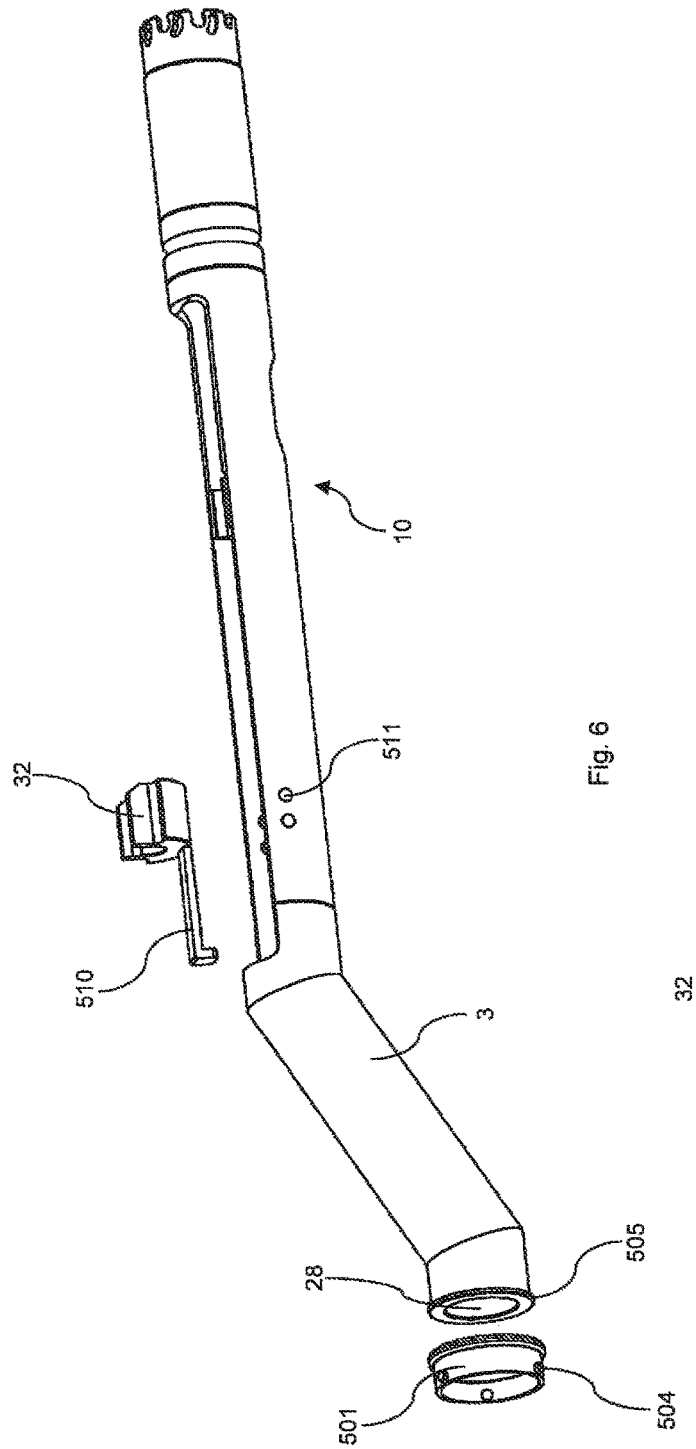
FIG. 6 is an exploding view of main components of the housing assembly of the reamer driver, showing a part of the sliding mechanism and bayonet sleeve of the remote release mechanism.

Now referring FIG. 6, the main components of the housing assembly 10 of the reamer driver 1 are shown. The distal transmission drive chain bearing 32 has an elongated hook 510 that is actuatable by the remote release sleeve 500 to translate the transmission drive train 21 and therefore the reamer head 4.

Figure 7B:
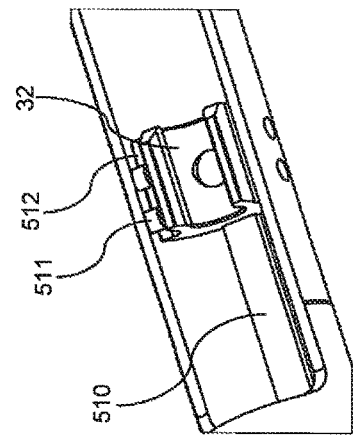
FIG. 7B is a detail of FIG. 6 in its assembled state showing the sliding mechanism of the remote release mechanism.
Figure 7A:
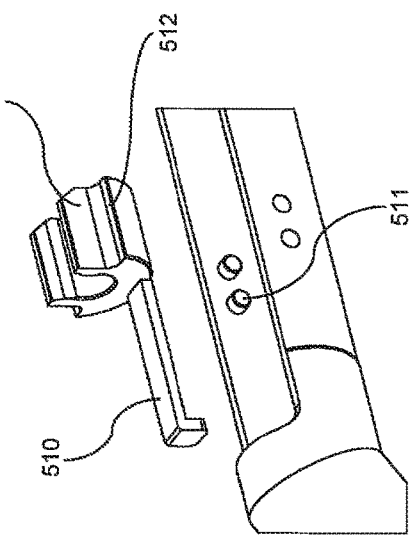
FIG. 7A is a detail of FIG. 6 showing the sliding mechanism of the remote release mechanism.

Now referring FIG. 7A and FIG. 7B, pins 511 retain the distal transmission drive chain bearing 32 in the body 3 while allowing it to slide backward/forward. Pins 511 slidingly contact the surface 512 of the distal transmission drive chain bearing 32.

Figure 8:
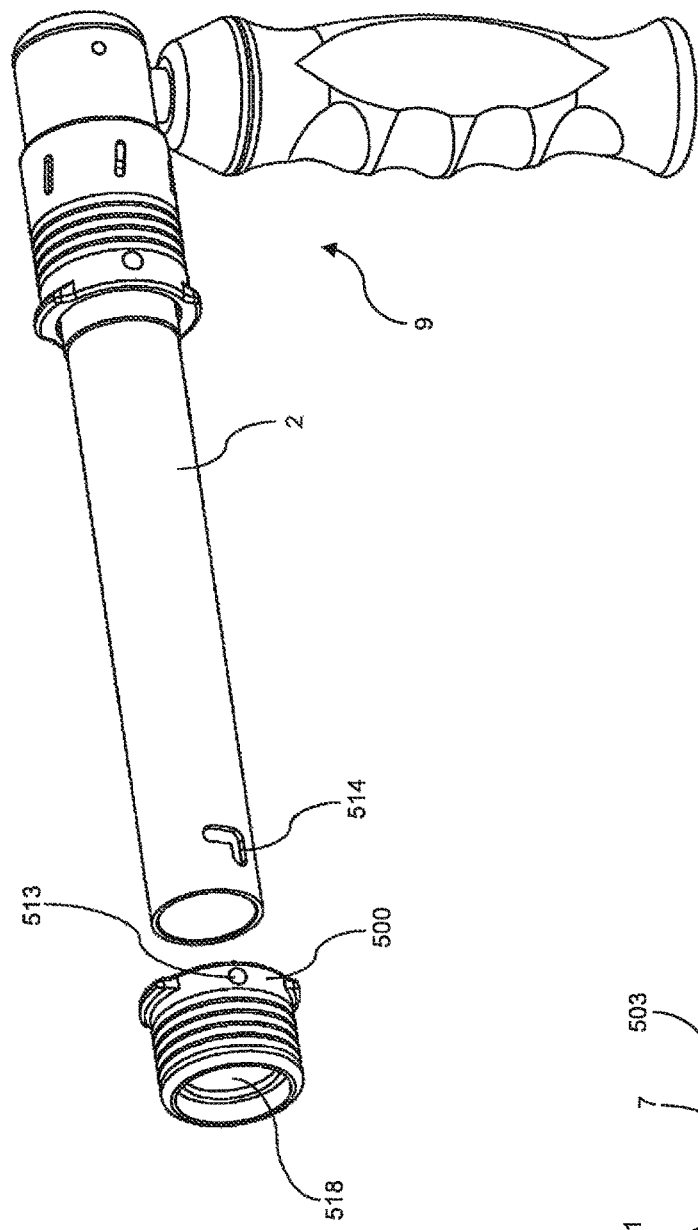
FIG. 8 is an exploding view of main components of the handle assembly of the reamer driver, showing the remote release sleeve of the remote release mechanism.

Now referring FIG. 8, the remote release sleeve 500 of the handle assembly 9 has a bearing surface 518 that slides onto the proximal tube 2 of the handle assembly 9. The bearing surface 518 may be made for example out of PEEK, carbon fiber PEEK, Teflon, PPSU or metal. The remote release sleeve 500 has a pin 513 which slides in the groove 514 of the proximal tube 2 in order to limit its amount of travel. In the preferred embodiment, the groove 514 has an L-shape geometry such that when the connector 120 is in the lock position, the user is forced to push the sleeve forward to unlock the reamer 227 forcing the user to first rotate the remote release sleeve before being able to push it forward. A spring 508 (shown in FIG. 10) biases the sleeve 540 toward the proximal end of the reamer driver 1. This also ensures that when the reamer driver 1 is inserted into soft tissue, the reamer 227 does not unlock inadvertently. In a different embodiment, the geometry of the groove 514 can be straight. A spring (not shown) can be used to spring load the remote release sleeve 500 in its backward position.

Figure 9:
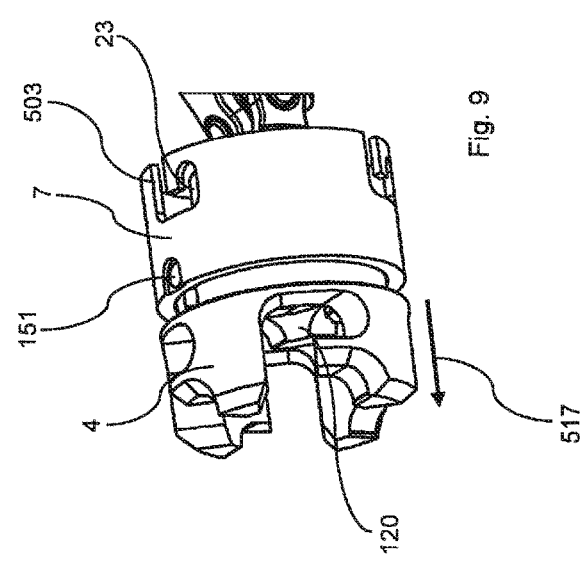
FIG. 9 is a partially assembled, detailed view of the surgical tool connector in its opened position.

Now referring to FIG. 9, the surgical tool connector is shown in its opened position. The transmission drive chain 21 and its reamer driver head 4 are in a forward position, while the cutting tool locking mechanism (ring 7, pin 151 and central cutting tool connection 120) are maintained in position by the bayonet sleeve 501, thereby releasing the cutting tool.

Figure 10:
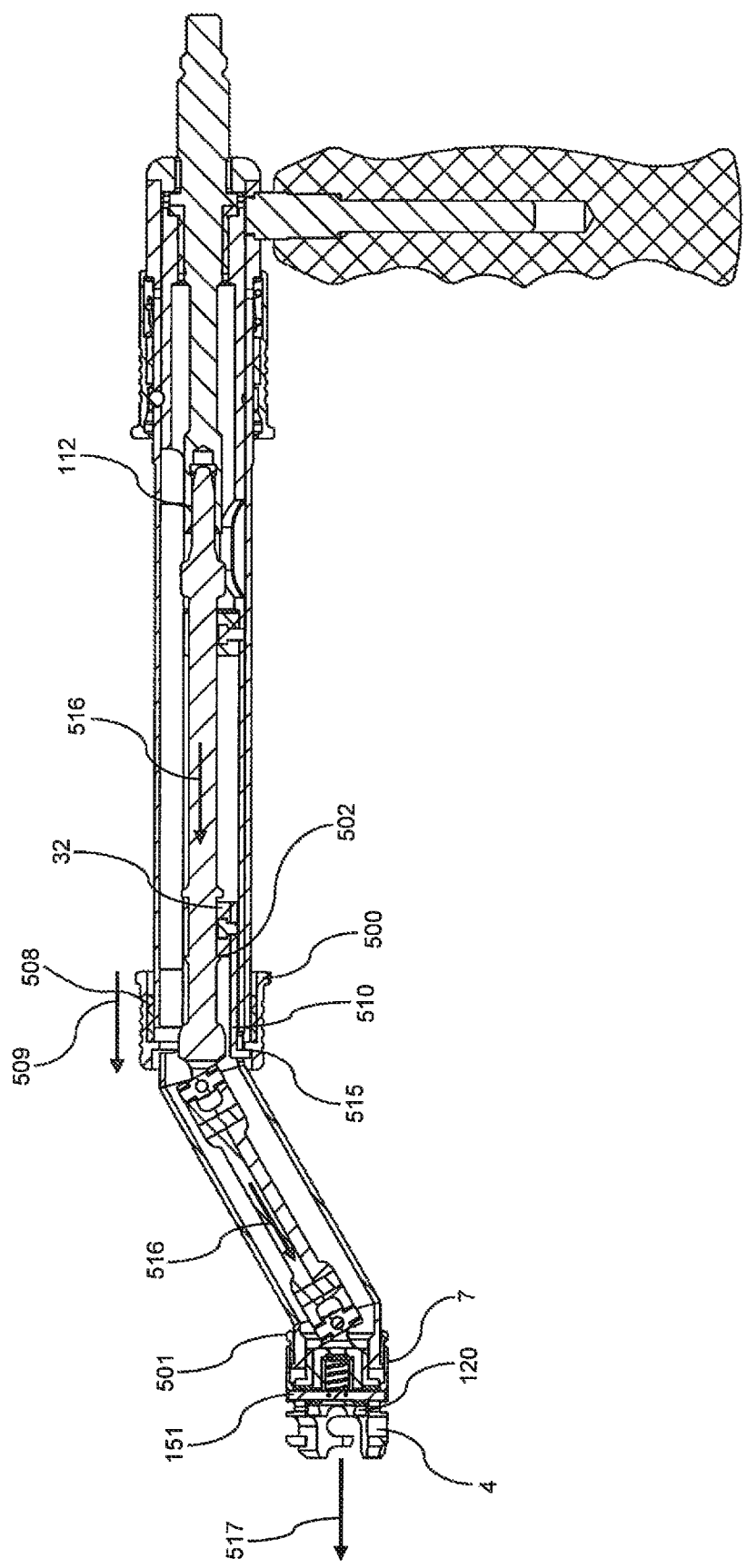
FIG. 10 is a cross-section view of the fully assembled reamer driver with the surgical tool connector in its opened position.

Now referring to FIG. 10, the remote release sleeve 500 is moved in its forward position 509, driving the distal transmission drive chain bearing 32 forward through its elongated book S10 at a contact point 515. The distal transmission drive chain bearing 32, through the contact point 502 then translates the transmission drive chain 21 in its forward (arrows 516 and 517) as well. The reamer driver head 4, being attached to the transmission drive chain 21, moves as well in its forward position 517, while the cutting tool locking mechanism (ring 7, pin 151 and central cutting tool connection 120) is maintained in position by the bayonet sleeve 510. The cutting tool 227 is therefore released. The cutting tool locking mechanism is spring loaded with spring 121 and therefore moves back to its closed position when the remote release sleeve 500 is relaxed.

Figure 11:
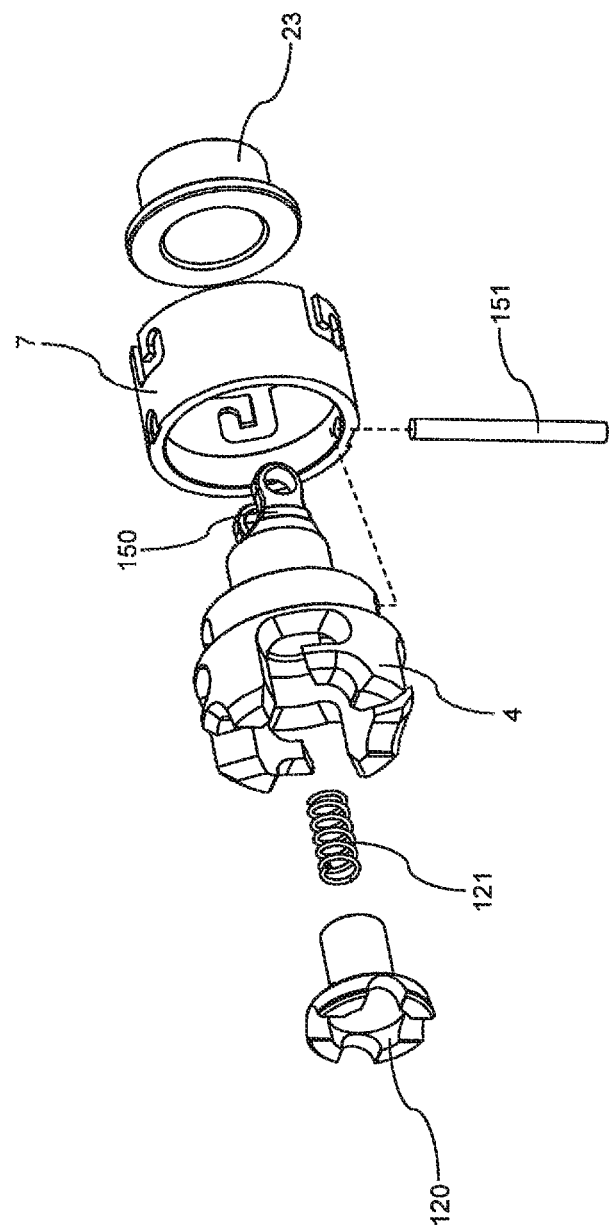
FIG. 11 is a detailed exploding view of the reamer head portion.

Now referring to FIG. 11, a retaining flange 505 allows the retention of the head bearing 23 once assembled onto the reamer head 4. This retaining flange 505 is positioned in such way to allow a slight translational movement of the head bearing 23 for easier cleaning while preventing the head bearing 23 from falling off. The pin 151 connects the ring 7 with the central cutting tool connection 120. The cutting tool locking mechanism (ring 7, pin 151 and central cutting tool connection 120) is able to slide backward/forward with respect to the reamer driver head 4 in order to release/lock the cutting tool. The cutting tool locking mechanism is spring loaded with spring 121 which biases the mechanism in its locked position.

Figure 12:
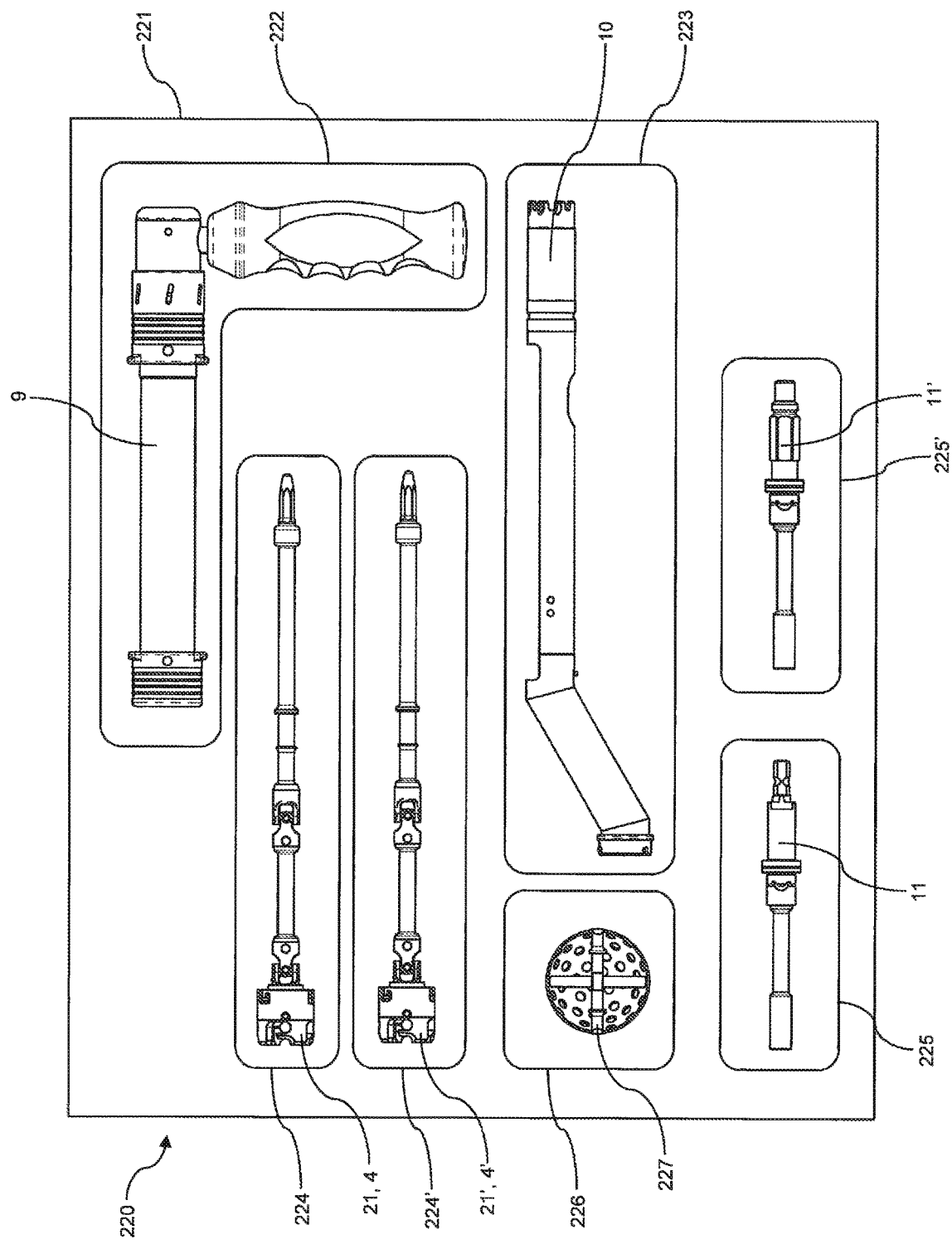
FIG. 12 is a kit of the invention.

Referring now to FIG. 12, a kit 220 includes the surgical reamer driver and its components (including some alternate components for alternate configurations), and in addition, a case 221 for organizing and storing the components of the kit. The surgical kit 220 further includes surgical tools 227 (one shown here by duplicates and others having differed outside diameters may be provided) of various sizes and styles, adapted to interface with the surgical tool connector 4. Optionally, an alternative motor coupling 11' may be provided, having an alternative connection configuration. Optionally, alternate transmission drive trains 21 and 21' are provided as well, each having an alternate surgical tool connector 4, 4'.

Figure 13:
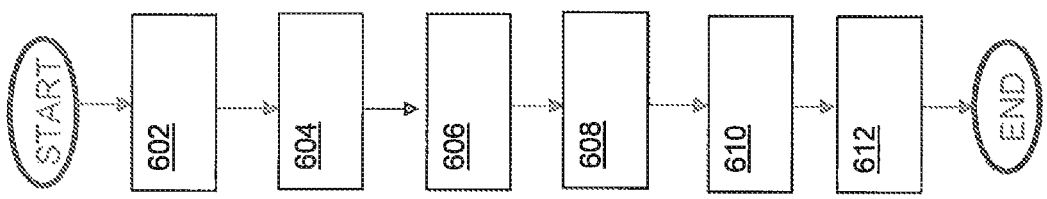
FIG. 13 is a flow chart of the method of the invention.

Referring now to FIG. 13, the method 600 of the invention includes several steps. In a first step 602, the drive train is inserted into the housing, thus assembling the drive train inside the housing. In a second step 604, the drive train is snapped into the distal transmission drive chain bearing 32. In a third step 606, the motor shaft coupling 11 is inserted into the housing thereby locking the drive train via axial constraint on one end. In a fourth step 608, the handle assembly is slid onto of the housing thereby effectively encapsulating the drive train. In a fifth step 610, the sliding release sleeve 8 is actuated to lock the handle assembly 9 to the housing 10. In a sixth step 612, the remote release sleeve 500 is actuated in order to connect the cutting tool to the reamer driver head 4.

The invention is best summarized by the following feature sets:

1. A surgical reamer driver having a transmission drive chain comprised of a locking surgical tool connector, a housing assembly enclosing the transmission drive chain, and a handle assembly, wherein the driver further includes a device for remotely inducing relative movement of the transmission drive chain with respect to at least a portion of the housing assembly to activate locking and unlocking of the locking surgical tool connector.
2. The surgical driver of feature set 1, wherein the device for remotely inducing relative movement of the transmission drive chain moves the transmission drive chain in a direction of at least one of the axes of the transmission drive chain.
3. The surgical reamer driver of feature set 1, wherein the device for remotely inducing relative movement includes a remote release sleeve, the remote release sleeve being releasably connected to the transmission drive chain, wherein the actuation of the remote release sleeve axially moves the transmission drive chain to open the surgical tool connector.
4. The surgical reamer driver of feature set 1, wherein the surgical tool connector has a release sleeve rotatably connected to the housing assembly.
5. The surgical reamer driver of feature set 1, where the proximal portion of the transmission drive chain and the surgical tool connector are not coaxial.
6. The surgical reamer driver of feature set 4, wherein the release sleeve is connected to the housing assembly via a bayonet sleeve, the bayonet sleeve being affixed to the housing assembly.
7. The surgical reamer driver of feature set 3, wherein the remote release sleeve interacts with a bearing holding at least a portion of the transmission drive chain into the housing assembly.
8. The surgical reamer driver of feature set 3, where at least one bearing holds at least a portion of the transmission drive chain into the housing assembly, wherein the remote release sleeve interacts with the said bearing to induce relative movement of the transmission drive chain
9. The surgical reamer driver of feature set 7, wherein the remote release sleeve interacts with the bearing via a connection such as an elongated hook or a pin.
10. The surgical reamer driver of one of feature sets 7 to 9, wherein the bearing is guided by guiding means, allowing it to slide in backward and forward direction within the housing assembly.
11. The surgical reamer driver of feature set 10, wherein the guiding means are a pair of pins, preferably one pair on each side of the bearing.
12. The surgical reamer driver of feature set 9, wherein the bearing is guided by guiding means adjacent to the connection such as the elongated hook or the pin.
13. The surgical reamer driver of feature set 6, wherein the remote release sleeve is positioned on a proximal tube at its distal end, preferably on the handle assembly.
14. The surgical reamer driver of feature set 6, wherein the remote release sleeve is positioned proximally on a proximal tube, preferably on the handle assembly.
15. The surgical reamer driver of feature set 6, wherein the bearing, the housing assembly and the remote release sleeve are adapted in operation to not open gaps thereby avoiding the entry of debris or chips.
16. The surgical reamer driver of feature set 15, wherein the surgical reamer driver remains fully encapsulated in operation in that the housing assembly and the remote release sleeve are adapted in operation to not open gaps, thereby avoiding the entry of debris or chips.
17. The surgical reamer driver of feature set 15, wherein the surgical reamer further includes a supplementary bearing holding the transmission drive chain into the housing assembly.
18. The surgical reamer driver of feature set 1, wherein the driver further includes a motor shaft coupling rotatably connecting the interfacing transmission drive chain, the motor shaft coupling providing a connection to a drive motor at a proximal end of thereof.
19. The surgical reamer driver of feature set 1, wherein the surgical tool connector includes a quick connect mechanism for coupling with a surgical tool.
20. The surgical reamer driver of feature set 1 further including a sliding release sleeve located on the housing assembly which respectively locks and unlocks the housing assembly for assembling or disassembling of the handle assembly from the housing assembly.
21. The surgical reamer driver of feature set 1, wherein a release sleeve remote to the reamer head slides on the handle assembly.
22. The surgical reamer driver of feature set 1, wherein the transmission drive chain includes at least one universal joint.
23. The surgical reamer driver of feature set 4, wherein the release sleeve is connected to the housing assembly by a quick connect mechanism having a bayonet connection.
24. A surgical kit comprising the surgical reamer driver of feature set 1 together with other components, the kit further comprising a case for organizing and storing the components of the kit.
25. The surgical kit of feature set 24, further including:
   a. surgical tools of various sizes and styles, adapted to interface with the surgical tool connector;
   b. optionally, an alternative motor coupling having an alternative connection configuration; and
   c. optionally, an alternate transmission drive chain having an alternate surgical tool connector.
26. A method for using a reamer driver including the steps of:
   a. inserting the transmission drive chain into the housing assembly, thus assembling the drive chain inside the housing assembly.
   b. snapping the transmission drive chain into the distal transmission drive chain bearing and, optionally, into the proximal transmission drive chain bearing; and
   c. inserting a motor shaft coupling into the housing assembly thereby avoiding axial force being transmitted into the drive chain from one end;
   d. sliding the handle assembly onto the housing assembly thereby effectively encapsulating the drive chain;
   e. actuating a sliding release sleeve to lock the handle assembly to the housing assembly;
   f. attaching a surgical tool to the reamer driver; and
   g. actuating the remote release sleeve remote to a reamer head to disconnect the surgical tool from the surgical tool connector.

In an advantage, the present invention provides a driver which has a means for remotely connect or disconnect (release) the reamer without having to manipulate a release sleeve located in the close area of the surgical tool connector.

In another advantage, the present invention provides a simple reamer driver connection that allows for the quick connect of different type of acetabular reamers from the center of the driver. In comparison to the existing reamer driver connections described in the prior art, the locking mechanism located in the center of the driver prevent debris and bone chips from entering into the mechanism and potentially disconnect the reamer from the reamer driver. It also reduces soft tissue irritation while rotating by limiting the sharp edges of components located around the head of the reamer driver.

In another advantage, the invention provides an easy to assemble and disassemble reamer driver connection for better cleaning and sterilization. The number of components and the risk that parts could be lost have been minimized.

It will be understood that the particular method and devices embodying the invention are shown by way of illustration and not as a limitation of the invention. Although certain illustrative embodiments of the invention have been shown and described here, a wide range of modification, changes and substitutions is contemplated in the foregoing disclosure.

Further, the invention should be considered as comprising all possible combinations of every feature described in the instant specification, appended claims, and/or drawing figures which may be considered new, inventive and industrially applicable.

It should be appreciated that the particular implementations shown and herein described are representative of the invention and its best mode and are not intended to limit the scope of the present invention in any way.

As will be appreciated by skilled artisans, the present invention may be embodied as a system, a device, or a method.

Moreover, the system contemplates the use, sale and/or distribution of any goods, services or information having similar functionality described herein.

The specification and figures should be considered in an illustrative manner, rather than a restrictive one and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "includes", "comprising", or variations thereof, are intended to refer to a non-exclusive listing of elements, such that any apparatus, process, method, article, or composition of the invention that includes a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification, inclusive of the appendix hereto and any computer program comprised therein.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A surgical reamer driver having a transmission drive chain comprising at least two axes, a locking surgical tool connector, a first and at least one further universal joint connecting at least one intermediate shaft with at least one proximal transmission shaft of the transmission drive chain, a housing assembly enclosing the transmission drive chain, at least one bearing mounted between the housing assembly and the transmission drive chain, and a handle assembly, wherein the driver further includes a release sleeve engaging with the at least one proximal transmission shaft of the transmission drive chain so as to be able to induce movement relative of the housing assembly to the transmission drive chain, the induced relative movement of the transmission drive chain with respect to at least a portion of the housing assembly activating locking and unlocking of the locking surgical tool connector.

2. The surgical driver of claim 1, wherein the release sleeve moves the transmission drive chain in a direction of at least one of the axes of the transmission drive chain.

3. The surgical reamer driver of claim 1, wherein actuation of the release sleeve axially moves the transmission drive chain to open the surgical tool connector.

4. The surgical reamer driver of claim 3, wherein the release sleeve interacts with at least one of the at least one bearing holding at least a portion of the transmission drive chain into the housing assembly.

5. The surgical reamer driver of claim 3, wherein the at least one bearing holds at least a portion of the transmission drive chain into the housing assembly, and wherein the remote release sleeve interacts with the said bearing to induce relative movement of the transmission drive chain.

6. The surgical reamer driver of claim 4, wherein the release sleeve interacts with at least one of the at least one bearing via an elongated hook or a pin.

7. The surgical reamer driver of claim 4, wherein the bearing is guided by a guide so as to slide in backward and forward direction within the housing assembly.

8. The surgical reamer driver of claim 7, wherein the guide is a pair of pins.

9. The surgical reamer driver of claim 8, wherein one of each pair of pins is mounted on each side of the bearing.

10. The surgical reamer driver of claim 7, wherein the guide is proximate to the elongated book or the pin.

11. The surgical reamer driver of claim 1, wherein the release sleeve is rotatably connected to the housing assembly.

12. The surgical reamer driver of claim 11, wherein the release sleeve is connected to the housing assembly via a bayonet sleeve, the bayonet sleeve being affixed to the housing assembly.

13. The surgical reamer driver of claim 12, wherein the release sleeve is positioned on a proximal tube at its distal end.

14. The surgical reamer driver of claim 12, wherein the release sleeve is positioned proximally on a proximal tube.

15. The surgical reamer driver of claim 12, wherein the at least one bearing, the housing assembly and the release sleeve are adapted in operation to not open gaps thereby avoiding the entry of debris or chips.

16. The surgical reamer driver of claim 15, wherein the surgical reamer driver remains fully encapsulated in operation in that the housing assembly and the release sleeve are adapted in operation to not open gaps, thereby avoiding the entry of debris or chips.

17. The surgical reamer driver of claim 15, wherein the surgical reamer further includes a supplementary bearing holding the transmission drive chain into the housing assembly.

18. The surgical reamer driver of claim 11, wherein the release sleeve is connected to the housing assembly by a quick connect mechanism having a bayonet connection.

19. The surgical reamer driver of claim 1, wherein the at least one proximal transmission shaft of the transmission drive chain and the locking surgical tool connector are not coaxial.

20. The surgical reamer driver of claim 1, wherein the driver further includes a motor shaft coupling rotatably connecting with the transmission drive chain, the motor shaft coupling providing a connection to a drive motor at a proximal end of thereof.

21. The surgical reamer driver of claim 1, wherein the surgical tool connector includes a quick connect mechanism for coupling with a surgical tool.

22. The surgical reamer driver of claim 1 further including a sliding release sleeve located on the housing assembly which respectively locks and unlocks the housing assembly for assembling or disassembling of the handle assembly from the housing assembly.

23. The surgical reamer driver of claim 1, wherein the release sleeve is remote to the locking surgical tool connector and slides on the handle assembly.

24. A surgical kit comprising the surgical reamer driver of claim 1, the kit further comprising a case for organizing and storing the components of the kit.

25. The surgical kit of claim 24, further including:
a) surgical tools of various sizes and styles, adapted to interface with the surgical tool connector;
b) an alternative motor coupling having an alternative connection configuration; and)) an alternate transmission drive chain having an alternate surgical tool connector.

26. A method of assembling the reamer driver of claim 1, the method including the steps of:
a) inserting the transmission drive chain into the housing assembly, thus assembling the drive chain inside the housing assembly;
b) snapping the transmission drive chain into the distal transmission drive chain bearing and into the proximal transmission drive chain bearing;
c) inserting a motor shaft coupling into the housing assembly thereby avoiding axial force being transmitted into the drive chain from one end;
d) sliding the handle assembly onto the housing assembly thereby effectively encapsulating the drive chain;
e) actuating a sliding release sleeve to lock the handle assembly to the housing assembly;
f) attaching a surgical tool to the reamer driver; and
g) actuating the remote release sleeve remote to a reamer head to disconnect the surgical tool from the surgical tool connector.

* * * * *